United States Patent [19]

Treuner et al.

[11] 4,096,330
[45] Jun. 20, 1978

[54] 7β-[[[(2-CYANOMETHYL)AMINO]-1,2-DIOX-OETHYL]AMINO]ACYL CEPHALOSPORINS

[75] Inventors: Uwe D. Treuner; Hermann Breuer, both of Regensburg, Germany

[73] Assignee: E. R. Squibb & Sons, Inc., Princeton, N.J.

[21] Appl. No.: 789,467

[22] Filed: Apr. 21, 1977

[51] Int. Cl.² .......................................... C07D 501/36
[52] U.S. Cl. .................................. 544/26; 260/465.4; 544/21; 544/27; 544/4
[58] Field of Search ...................... 544/19, 21, 26, 27, 544/30, 4

[56] References Cited

U.S. PATENT DOCUMENTS

| 3,573,294 | 3/1971 | Long et al. | 260/243 C |
| 3,997,533 | 12/1976 | Kabbe et al. | 260/243 C |
| 4,028,354 | 6/1977 | Breuer et al. | 260/243 C |

Primary Examiner—Donald G. Daus
Assistant Examiner—David E. Wheeler
Attorney, Agent, or Firm—Lawrence S. Levinson; Merle J. Smith

[57] ABSTRACT

7β-[[[(2-Cyanomethyl)amino]-1,2-dioxoethyl]amino]-acyl cephalosporins which have the formula

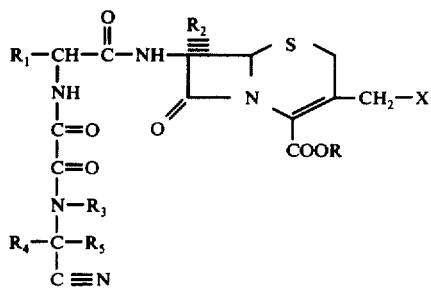

wherein R is hydrogen, lower alkyl, phenyl-lower alkyl, diphenyl-lower alkyl, tri(lower alkyl)silyl, tri(lower alkyl)stannyl, trihaloethyl or a salt forming ion; $R_1$ is hydrogen, lower alkyl, saturated or unsaturated cycloalkyl, phenyl, phenyl-lower alkyl, substituted phenyl or certain heterocyclic groups; $R_2$ is hydrogen or methoxy; $R_3$ is hydrogen, lower alkyl, phenyl-lower alkyl or cycloalkyl; $R_4$ and $R_5$ each is hydrogen or lower alkyl; and X is hydrogen, lower alkanoyloxy, carbamoyloxy, lower alkoxy, lower alkylthio

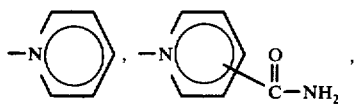

or certain heterothio groups, are useful as antibacterial agents.

13 Claims, No Drawings

7β-[[[(2-CYANOMETHYL)AMINO]-1,2-DIOXOETHYL]AMINO]ACYL CEPHALOSPORINS

SUMMARY OF THE INVENTION

Cephalosporins and penicillins having a ureido and similar type acyl side chain are disclosed, for example, in U.S. Pat. Nos. 3,673,183, 3,687,949, 3,708,479, 3,833,568, 3,860,591, 3,925,368, 3,954,802, 3,956,292, 3,972,870, 3,974,140, 3,982,011 and German Offenlegungsschrift Nos. 2,513,954 and 2,514,019. Cephalosporins having various acyl side chains and a 7α-methoxy sustituent are shown in various U.S. patents including, for example, U.S. Pat. Nos. 3,775,410, 3,780,031, 3,780,033, 3,780,034, 3,780,037 and 3,843,641, etc. 7β-[(2-amino-1,2-dioxoethyl)amino]acyl cephalosporins are described in our copending application Ser. No. 776,400 filed Mar. 10, 1977.

This invention relates to new 7β-[[[(2-cyanomethyl)amino]-1,2-dioxoethyl]amino]acyl cephalosporin derivatives which have the formula

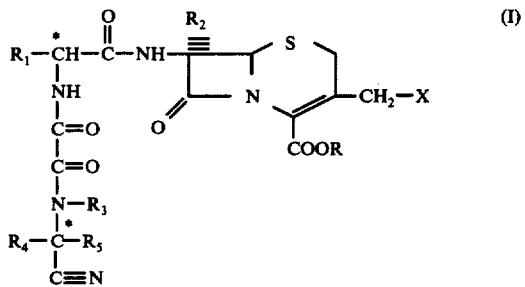

which are distinguishable from such prior known compounds.

R represents hydrogen, lower alkyl, phenyl-lower alkyl, diphenyl-lower alkyl, tri(lower alkyl)silyl, tri(-lower alkyl)stannyl, trihaloethyl or a salt forming ion.

$R_1$ represents hydrogen, lower alkyl, saturated or unsaturated cycloalkyl, phenyl, phenyl-lower alkyl, substituted phenyl or certain heterocyclic groups.

$R_2$ represents hydrogen or methoxy. The $R_2$ substituent is in the α-configuration as indicated by the broken lines.

$R_3$ represents hydrogen, lower alkyl, phenyl-lower alkyl or cycloalkyl.

$R_4$ and $R_5$ each represents hydrogen or lower alkyl.

X represents hydrogen, lower alkanoyloxy, carbamoyloxy, lower alkoxy, lower alkylthio, certain heterothio groups,

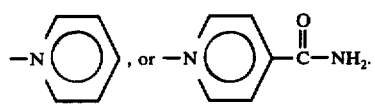

When X is pyridinium or carbamoyl substituted pyridinium, the compounds can be structurally represented as having the formula

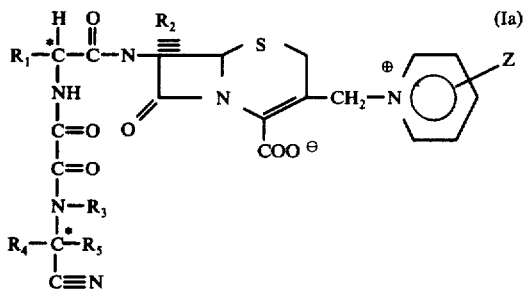

wherein Z is hydrogen or carbamoyl.

The asterisks indicate asymmetric carbon atoms.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 7 carbon atoms, preferably 1 to 4 carbons, and especially 1 or 2 carbons. Examples of the type of groups contemplated are methyl, ethyl, propyl, isopropyl, butyl, t-butyl, etc. The lower alkoxy and lower alkylthio groups include such lower alkyl groups attached to an oxygen or sulfur, respectively, e.g., methoxy, ethoxy, propoxy, methylthio, ethylthio, propylthio, etc. The phenyl-lower alkyl and diphenyl-lower alkyl groups include such lower alkyl groups attached to one or two phenyl rings, preferably benzyl, phenethyl and diphenylmethyl.

The saturated and unsaturated cycloalkyl groups are the alicyclic groups having up to 7 carbons and up to 2 double bonds in the ring, i.e., the cycloalkyl groups cyclopropyl, cyclobutyl, cyclopentyl, cyclohexyl and cycloheptyl, the cycloalkenyl groups having up to 7 carbons with one double bond, cyclobutenyl, cyclopentenyl, cyclohexenyl and cycloheptenyl and the cycloalkadienyl groups having up to 7 carbons with two double bonds located at various positions such as 1,4-cyclohexadienyl which is especially preferred.

The substituted phenyl groups include one or two substituents selected from halogen (preferably chlorine or bromine), lower alkyl (preferably having 1 to 4 carbons, especially methyl or ethyl), lower alkoxy (preferably having 1 to 4 carbons especially methoxy or ethoxy), and hydroxy, e.g., 2-, 3-, or 4-chlorophenyl, 2-, 3-, or 4-bromophenyl, 2-, 3-, or 4-hydroxyphenyl, 3,5-dichlorophenyl, 2-, 3-, or 4-methylphenyl, 2-, 3- or 4-ethoxyphenyl, etc.

The salt forming ions represented by R are metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)silyl group.

The heterocyclic groups represented by $R_1$ are thienyl, furyl or pyridyl, i.e., 2-thienyl, 3-thienyl, 2-furyl, 3-furyl, 2-pyridyl, 3-pyridyl or 4-pyridyl.

Lower alkanoyloxy refers to a group of the formula

preferably wherein the lower alkyl group is methyl. The lower alkanoyloxy groups have up to seven carbons of which those having up to 4 carbons are preferred and acetyloxy is especially preferred.

The heterothio groups represented by X are

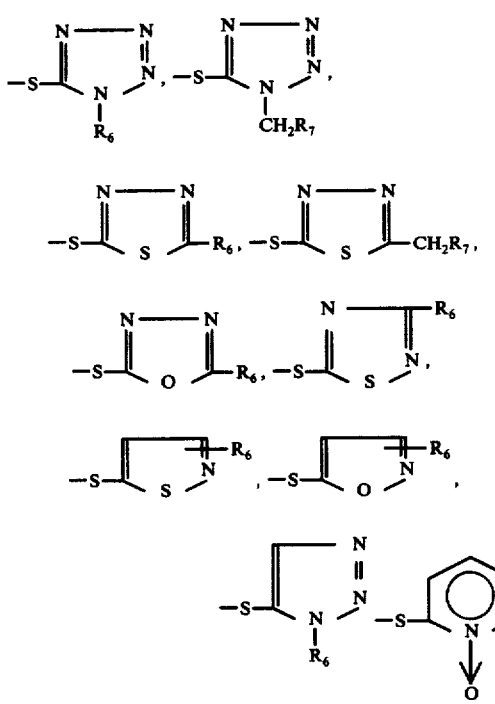

wherein $R_6$ is hydrogen or lower alkyl (preferably having 1 to 4 carbons especially methyl or ethyl). $R_6$ is preferably hydrogen.

$R_7$ is carboxy (COOH) or the ion-COO $\ominus$ ion $\oplus$, —COO-lower alkyl, —SO$_3$H, —SO$_2$-lower alkyl or cyano.

The products of this invention are produced by acylating a cephem compound having the formula

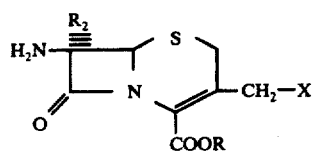

with an acid having the formula

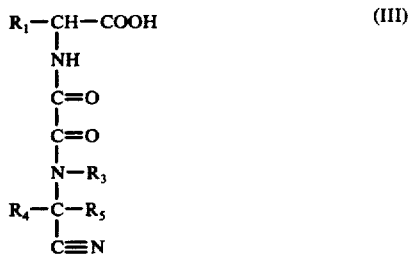

or an activated derivative like the acid halide, activated ester like the nitrophenyl ester or dinitrophenyl ester, or mixed anhydride, and/or in the presence of a coupling agent like dicyclohexylcarbodiimide.

The compound of formula II is preferably in the form of an ester, i.e., R is an easily removable group like diphenylmethyl, which is preferred, t-butyl, trimethylsilyl, etc.

One preferred synthesis comprises reacting the acid of formula III first with chloroformic acid alkyl ester in the presence of a base like triethylamine and then with the diphenylmethyl ester of the compound of formula II. The resulting ester is then hydrolyzed with trifluoroacetic acid and anisole to obtain the free carboxyl group in the 4-position. A salt can be obtained from the acid by reaction with the base having the desired cation.

This reaction can be carried out, for example, by dissolving or suspending the acid in an inert organic solvent such as chloroform, tetrahydrofuran, methylene chloride, dioxanne, benzene or the like, and adding, at a reduced temperature of about 0°–5° C., using about an equimolar amount of the compound of formula II. The product of the reaction is then isolated by conventional procedures, e.g., by concentration or evaporation of the solvent.

According to an alternate method a compound having the formula

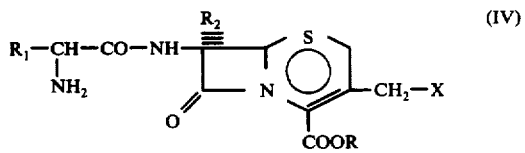

preferably in the form of a salt like the trifluoroacetic acid salt, is dissolved or suspended in an organic solvent such as acetonitrile, methylene chloride, chloroform, dimethylformamide, tetrahydrofuran, dioxane, benzene or the like, and converted to an ester, for example forming the trimethylsilyl ester by reaction with bis(trimethylsilyl)acetamide. The product is then made to react with a compound having the formula

wherein hal represents a halogen, preferably chlorine, in an organic solvent like those mentioned above at a reduced temperature, e.g., about 0° C. and in the presence of a neutral acid scavenger like propylene oxide, butylene oxide or the like.

The compounds of formula I wherein X is pyridinium or carbamoyl substituted pyridinium can be prepared by reacting a compound of formula I wherein X is acetoxy with pyridine or carbamoyl substituted pyridine in a polar solvent such as water and in the presence of a catalyst such as an alkali metal thiocyanate by the method described in U.S. Pat. No. 3,792,047 and German Offenlegungsschrift No. 2,234,280.

Compounds of formula I wherein X is a heterothio group can also be produced by first producing a compound of formula I wherein X is acetoxy and then reacting this product with a mercaptan of the formula

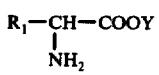   (VI)

or an alkali metal (preferably sodium) salt of the formula hetero-S-alkali metal   (VII)

by the methods described in U.S. Pat. Nos. 3,855,213; 3,890,309; and 3,892,737.

The starting material of formula III is produced from an α-amino acid ester having the formula

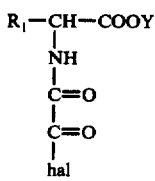   (VIII)

wherein $R_1$ has the same meaning as defined above and Y is a readily removable group, e.g., diphenylmethyl, nitrophenyl, dinitrophenyl, t-butyl, trimethylsilyl or the like, which is made to react with an oxalyl halide like oxalyl chloride to form an intermediate having the formula

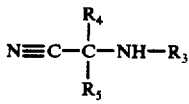   (IX)

wherein hal represents halogen, preferably chlorine, in a solvent like dioxane. This intermediate is then made to react with a compound having the formula

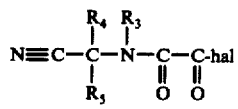   (X)

e.g., in an organic solvent like those mentioned above in the presence of an organic base like dimethylaniline at a reduced temperature, e.g., about −20° C, and treatment of this intermediate with an acid, e.g., trifluoroacetic acid and anisole, yields the free acid of formula III. By reacting the compound of formula X with an oxalyl halide like oxalyl chloride in a solvent like dioxane at an elevated temperature, e.g., about 60° to 70° C, a compound of formula V is obtained.

Alternatively, the starting material of formula III can be produced from the starting material of formula VIII by reacting the latter with a compound having the formula $$N\equiv C-\underset{\underset{R_5}{|}}{\overset{\overset{R_4}{|}}{C}}-N-\underset{\underset{O}{\|}}{\overset{\overset{R_3}{|}}{C}}-\underset{\underset{O}{\|}}{C}-hal \quad (V)$$

The carboxylate salts of the compound of formula I are formed by reacting the carboxyl group of the cephalosporanic acid moiety, i.e., R is hydrogen, with any of the salt forming ions described above.

It will be appreciated that the compounds of formula I are optically active due to the presence of asymmetric carbon atoms indicated by the asterisks. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and alkali metal salts of formula I (i.e. R is hydrogen, sodium or potassium) wherein X is acetoxy or heterothio especially 1-methyl-1H-tetrazol-5-ylthio; $R_1$ is cyclohexadienyl, phenyl or heterocyclic selected from 2-thienyl, 3-thienyl, 2-furyl, 3-furyl, 2-pyridyl, 3-pyridyl and 4-pyridyl; $R_2$ is hydrogen or methoxy especially hydrogen; and $R_3$, $R_4$ and $R_5$ each is hydrogen or lower alkyl, especially hydrogen, and especially the D-isomers thereof.

The most preferred final compounds are the acids and alkali metal salts of formula I wherein $R_1$ is 2-thienyl, or phenyl most especially 2-thienyl; $R_2$, $R_3$, $R_4$ and $R_5$ each is hydrogen; and X is heterothio particularly wherein X is

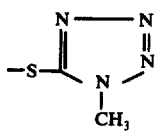

The acid compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter hafniae, Enterobacter cloacae, Klebsiella pneumoniae, Serratia marcescens*, etc. They may be used as antibacterial agents to combat infections due to organisms such as those named above, and in general may be utilized in a manner similar to cephradine and other cephalosporins. For example, a compound of formula I or a physiologically acceptable salt thereof may be used in various animal species in an amount of about 1 to 100 mg/kg., daily, orally or parenterally, in single or two to four divided doses to treat infections of bacterial origin, e.g., 5.0 mg/kg in mice.

Up to about 600 mg. of an acid compound of formula I or a physiologically acceptable salt thereof may be incorporated in an oral dosage form such as tablet, capsule or elixir or in an injectable form in a sterile aqueous vehicle prepared according to conventional pharmaceutical practice.

Illustrative process details are provided in the examples which are models by which additional members of the class can be prepared. Additional process details on the production of certain intermediates can also be found in our copending application identified above. All temperatures are in degrees Celsius.

EXAMPLE 1

[(Cyanomethyl)amino]oxoacetyl chloride 20 mM of cyanomethylamine hydrochloride and 25 mM of oxalyl chloride in 100 mM of absolute dioxane are heated at 60°–70° while passing through a stream of nitrogen. After one hour a clear solution results and there is no evidence of hydrogen chloride in the nitrogen stream. The solvent is evaporated under vacuum and the residual, light brown oil is taken up in methylene chloride, filtered over charcoal and stored at −30° until it is to be used.

EXAMPLE 2

D-α-[[[(Cyanomethyl)amino]oxoacetyl]amino]-2-thiopheneacetic acid, diphenylmethyl ester 10 mM of 2-D-thienylglycine, diphenylmethyl ester are dissolved in 20 ml. of methylene chloride, 10 mM of dimethylaniline are added and half the product of Example 1 is added dropwise with stirring at −20°. After 30 minutes, the reaction solution is washed first with 50 ml. of 1 N hydrochloric acid and then with 50 ml. of water. After drying over sodium sulfate, it is concentrated by evaporation. A viscous yellow mass is obtained which solidifies upon treatment with ether. This is crystallized from a little ethanol to obtain D-α-[[[(cyanomethyl)amino]-oxoacetyl]amino]-2-thiopheneacetic acid, diphenylmethyl ester in the form of white crystals, yield 63%, m.p. 160°–161°.

EXAMPLE 3

D-α-[[[(Cyanomethyl)amino]oxoacetyl]amino]-2-thiopheneacetic acid

By treating the diphenylmethyl ester obtained in Example 2 with trifluoroacetic acid and anisole (4:1) D-α-[[[(cyanomethyl)amino]oxoacetyl]amino]-2-thiopheneacetic acid is obtained in 74% yield. The product is recrystallized from absolute ethanol to obtain white crystals, m.p. 199°–200°.

EXAMPLE 4

7-β-[[D-[[2-[(Cyanomethyl)amino]-1,2-dioxoethyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid 10 mM of D-α-[[[cyanomethyl)amino]oxoacetyl]-amino]-2-thiopheneacetic acid and 10 mM of triethylamine are dissolved in 100 ml. of tetrahydrofuran, cooled to −5° and a solution of 11 mM of chloroformic acid ethyl ester is slowly added dropwise. This is permitted to react for 20 minutes and then a solution of 10 mM of 7-amino-2-[[(1-methyl-1H-tetrazol-5-yl)thio]methyl]cephalosporanic acid, diphenylmethyl ester in tetrahydrofuran is added. After stirring for eight hours at −5° and 1 hour at room temperature, the solution is concentrated under vacuum and then taken up with methylene chloride and water. The organic phase is washed with 2N phosphoric acid solution and water, dried, treated with charcoal and concentrated. The product, 7-β-[[D-[[2-[(cyanomethyl)amino]-1,2-dioxoethyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, is obtained as a solid brownish foam. By treating this with trifluoroacetic acid and anisole (4:1), 7-β-[[D-[[2-[(cyanomethyl)amino]-1,2-dioxoethyl]amino]-2-thienylacetyl]amino]3-[[(1-methyl-1H-tetrazol-5-yl)thio]methyl]-8-oxo-5-thia-1-azabicyclo[4.2.0]oct-2-ene-2-carboxylic acid is obtained in the form of a beige powder which is recrystallized from isopropanol/ethyl acetate, m.p. 154°.

EXAMPLE 5

Alternate synthesis of 7-β-[[D-[[2-[(Cyanomethyl)amino]-1,2-dioxoethyl]-amino]-2-thienylacetyl]amino]-3-[[(1-methyl-1H-tetrazol-5-yl)thio]methyl]-8-oxo-5-thia-1-azabicyclo[4.2.0-]oct-2-ene-2-carboxylic acid 10 mM of 7β-amino-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt are suspended in acetonitrile. After the addition of 3 ml. of bis(trimethylsilyl)acetamide and 15 mM of propylene oxide, a clear solution results in several minutes. This is cooled to 0° and 12 mM of chloroxoacetic acid, cyanomethylamide dissolved in methylene chloride is added dropwise. This is stirred for one hour and then the solvent is removed in vacuo. The residue is stirred for 1 hour in 300 ml. of ethyl acetate and 50 ml. of water. The organic phase is then dried, treated with charcoal and concentrated to 30 ml., whereupon the product 7-β-[[D-[[2-[(cyanomethyl)amino]-1,2-dioxoethyl]amino]-2-thienylacetyl]amino]-3-[[(1-methyl-1H-tetrazol-5-yl)thio]methyl-8-oxo-5-thia-1-azabicyclo[4.2.0]oct-2-ene-2-carboxylic acid crystallizes. By pouring the mother liquor into ether an additional quantity of product is obtained, m.p. 153°–155°.

EXAMPLE 6

7β-[[D-[[2-[(Cyanomethyl)amino]-1,2-dioxoethyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt By freeze drying an equimolar aqueous solution of the acid of Example 4 or Example 5 and sodium bicarbonate, 7β-[[D-[[2-[(cyanomethyl)amino]-1,2-dioxoethyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, sodium salt is obtained as a light yellow powder, m.p. 178° (dec.).

EXAMPLES 7–70

Following the procedure of Example 4 but employing the acylating agent A below having the substituents in the following table (which is prepared as described in Examples 1 to 3) and the 7β-aminocephalosporanic acid Compound B below, one obtains the product C having the same substituents shown in the table. Where appropriate, the protecting group and ester group are removed as in Example 4. The salts are produced as in Example 6.

| Example | R₁ | R₂ | R | R₃ | R₄ | R₅ | X |
|---|---|---|---|---|---|---|---|
| 7 | thienyl | H | t-C₄H₉ | H | H | H | -S-(5-methyl-1,3,4-thiadiazol-2-yl) |
| 8 | thienyl | H | H | H | CH₃ | H | -S-(5-methyl-1,3,4-thiadiazol-2-yl) |
| 9 | thienyl | -OCH₃ | -CH₂-phenyl | H | H | H | -S-(1-methyl-1H-tetrazol-5-yl) |
| 10 | thienyl | -OCH₃ | H | H | H | H | -S-(1-methyl-1H-tetrazol-5-yl) |
| 11 | thienyl | H | H | -CH₂-phenyl | H | H | -O-C(=O)-CH₃ |
| 12 | thienyl | H | H | -CH₂-phenyl | H | H | -S-(1-methyl-1H-tetrazol-5-yl) |
| 13 | phenyl | H | -CH(phenyl)₂ | CH₃ | CH₃ | H | -S-(1-methyl-1H-tetrazol-5-yl) |
| 14 | phenyl | -OCH₃ | H | H | H | H | -S-(1-methyl-1H-tetrazol-5-yl) |
| 15 | thienyl | H | -CH₂CCl₃ | C₂H₅ | H | H | -S-(1-ethyl-1H-tetrazol-5-yl) |
| 16 | thienyl | H | CH₃ | H | H | H | -S-(pyridyl N-oxide) |

-continued

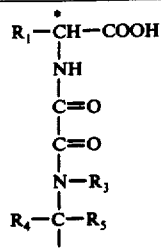
A

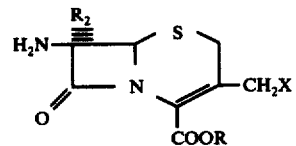
B

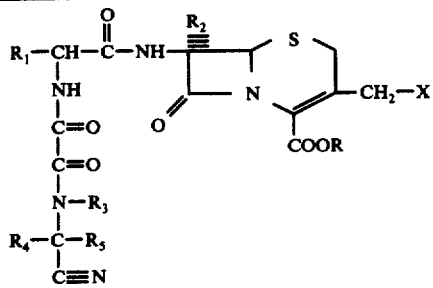
C

| Example | R₁ | R₂ | R | R₃ | R₄ | R₅ | X |
|---|---|---|---|---|---|---|---|
| 17 | phenyl | H | Na | H | H | $C_2H_5$ | 2-pyridylthio N-oxide |
| 18 | phenyl | $-OCH_3$ | $-CH(C_6H_5)_2$ | $C_2H_5$ | H | H | $-S-$(1-methyl-tetrazol-5-yl) |
| 19 | 2-pyridyl | H | H | H | $CH_3$ | $CH_3$ | $-S-$(1-methyl-tetrazol-5-yl) |
| 20 | 2-thienyl | H | H | H | H | H | $-O-CO-CH_3$ |
| 21 | 2-furyl | $-OCH_3$ | $-C_2H_5$ | $-CH_3$ | H | H | $-S-$(1-methyl-tetrazol-5-yl) |
| 22 | phenyl | H | H | $-CH_2-C_6H_5$ | H | H | $-O-CO-CH_3$ |
| 23 | 2-furyl | H | H | $CH_3$ | H | $CH_3$ | $-O-CO-CH_3$ |
| 24 | phenyl | H | H | $-C_2H_5$ | H | H | $-S-CH_3$ |
| 25 | phenyl | $-OCH_3$ | H | H | H | H | $-OCONH_2$ |
| 26 | phenyl | H | H | H | H | H | pyridinium |

-continued

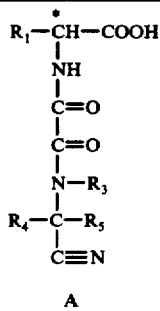
A

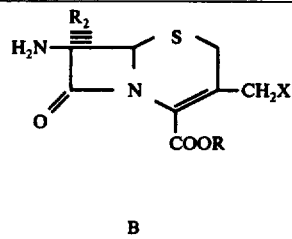
B

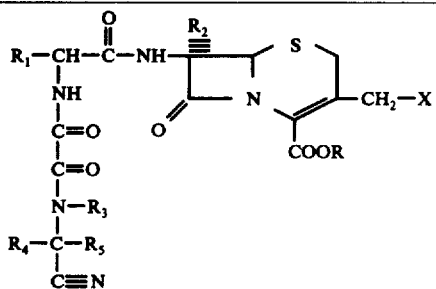
C

| Example | R₁ | R₂ | R | R₃ | R₄ | R₅ | X |
|---|---|---|---|---|---|---|---|
| 27 | 2-thienyl | $-OCH_3$ | H | H | H | H | nicotinamide (pyridine-CONH₂) |
| 28 | 2-furyl | H | K | H | H | H | $-S-$(1,3,4-thiadiazole) |
| 29 | 2-furyl | H | $Sn(CH_3)_3$ | $-CH_3$ | H | H | $-S-$(tetrazol-5-yl, NH) |
| 30 | 2-pyridyl | H | $t-C_4H_9$ | $-CH_3$ | H | H | $-OCH_3$ |
| 31 | 3-pyridyl | H | $-CH(C_6H_5)_2$ | H | H | H | $-S-$(1-methyl-tetrazol-5-yl) |
| 32 | 4-pyridyl | H | K | H | H | H | $-S-$(5-methyl-1,3,4-oxadiazol-2-yl) |
| 33 | H | H | $-(CH_2)_2C_6H_5$ | H | H | H | $-S-$(1,3,4-thiadiazol-2-yl) |
| 34 | $-C_2H_5$ | $-OCH_3$ | $t-C_4H_9$ | $-C_3H_7$ | H | H | $-O-\overset{O}{\underset{\|}{C}}-CH_3$ |
| 35 | phenyl | H | $-N(C_2H_5)_3$ | H | H | $-C_3H_7$ | H |
| 36 | phenyl | H | H | H | H | H | $-S-CH_3$ |
| 37 | cyclohexyl | H | $-CH(C_6H_5)_2$ | H | H | H | $-S-$(tetrazol-5-yl, NH) |

-continued

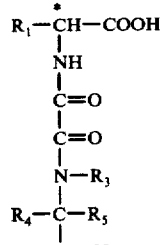
A

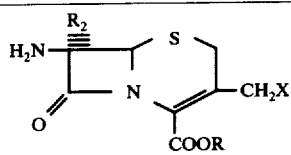
B

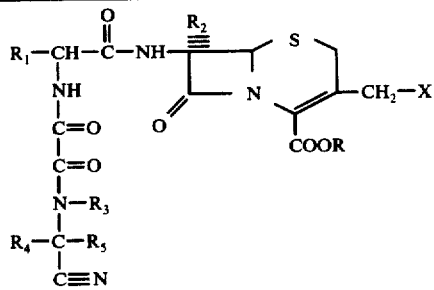
C

| Example | R₁ | R₂ | R | R₃ | R₄ | R₅ | X |
|---|---|---|---|---|---|---|---|
| 38 | cyclohexyl | $-OCH_3$ | H | H | $CH_3$ | H | $-OCH_3$ |
| 39 | cyclohexadienyl | H | $-CH(C_6H_5)_2$ | H | H | H | $-S-$ (5-ethyl-1,2,3,4-tetrazol-2-yl) |
| 40 | cyclohexadienyl | $-OCH_3$ | H | H | H | H | $-S-$ (1-methyl-1,2,3,4-tetrazol-5-yl) |
| 41 | cyclohexadienyl | H | $-CH(C_6H_5)_2$ | H | H | H | $-O-CO-CH_3$ |
| 42 | cyclohexadienyl | $-OCH_3$ | H | H | H | H | H |
| 43 | phenyl | H | K | cyclohexyl | H | H | $-O-CO-CH_3$ |
| 44 | 2-thienyl | H | H | cyclopentyl | H | H | H |
| 45 | cyclopentyl | H | $t\text{-}C_4H_9$ | H | H | H | $-S-$ (1-methyl-1,2,3,4-tetrazol-5-yl) |
| 46 | $C_6H_5(CH_2)_2-$ | H | H | H | H | H | $-S-$ (4-methyl-1,3,4-thiadiazol-2-yl) |
| 47 | cyclopentadienyl | H | H | $-CH_3$ | H | H | $-S-$ (1,3,4-oxadiazol-2-yl) |

-continued

| | | | | | | |
|---|---|---|---|---|---|---|
| A | | | B | | | C |

| Example | $R_1$ | $R_2$ | R | $R_3$ | $R_4$ | $R_5$ | X |
|---|---|---|---|---|---|---|---|
| 48 | cyclohexenyl | —OCH$_3$ | H | H | H | H | -S-(1,3,4-thiadiazol-2-yl)-5-CH$_3$ |
| 49 | cyclohexenyl | H | —CH(C$_6$H$_5$)$_2$ | H | H | H | -S-(1-methyl-tetrazol-5-yl) |
| 50 | 4-HO-C$_6$H$_4$- | H | —CH(C$_6$H$_5$)$_2$ | H | H | —C$_4$H$_9$ | -S-(1-methyl-tetrazol-5-yl) |
| 51 | 4-H$_3$C-C$_6$H$_4$- | H | —CH$_2$—CCl$_3$ | CH$_3$ | H | H | -S-(1,3,4-oxadiazol-2-yl) |
| 52 | 3,5-Cl$_2$-C$_6$H$_3$- | H | —CH(C$_6$H$_5$)$_2$ | H | H | H | -S-(1,3,4-thiadiazol-2-yl) |
| 53 | 4-H$_3$CO-C$_6$H$_4$- | H | H | H | H | H | -S-(1-methyl-tetrazol-5-yl) |
| 54 | 2-thienyl | H | —CH(C$_6$H$_5$)$_2$ | H | H | H | -S-(4-methyl-thiazol-2-yl) |
| 55 | C$_6$H$_5$- | —OCH$_3$ | —CH$_2$-C$_6$H$_5$ | CH$_3$ | H | H | -S-(1-ethyl-triazol-5-yl) |
| 56 | 2-thienyl | H | H | CH$_3$ | H | H | -S-(4-methyl-thiazol-2-yl) |
| 57 | 4-HO-C$_6$H$_4$- | H | H | —CH$_2$-C$_6$H$_5$ | H | —CH$_3$ | -S-(4-methyl-isoxazol-3-yl) |

-continued

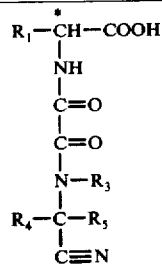
A

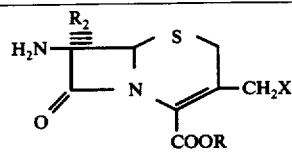
B

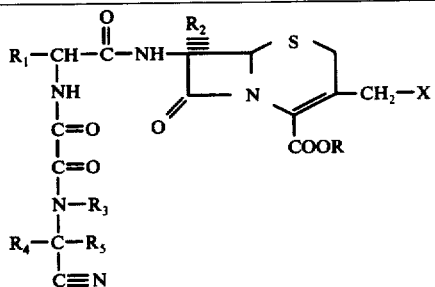
C

| Example | R₁ | R₂ | R | R₃ | R₄ | R₅ | X |
|---|---|---|---|---|---|---|---|
| 58 | thienyl | H | H | H | H | H | -S-(isothiazole) |
| 59 | phenyl | H | Na | H | H | H | -S-(thiadiazole) |
| 60 | phenyl | H | H | H | H | H | -S-(triazole-NH) |
| 61 | phenyl | H | H | H | H | H | $-S-C_2H_5$ |
| 62 | phenyl | $-OCH_3$ | $Si(CH_3)_3$ | H | H | H | -S-(1-methyltetrazole) |
| 63 | thienyl | $-OCH_3$ | H | H | H | H | $-OCONH_2$ |
| 64 | thienyl | H | H | H | H | H | $-OCONH_2$ |
| 65 | phenyl | H | H | H | H | H | -S-(1-CH₂COOH-tetrazole) |
| 66 | phenyl | $-OCH_3$ | H | H | H | $-CH_3$ | -S-(1-COO-C₂H₅-tetrazole) |
| 67 | thienyl | H | H | $-CH_3$ | H | H | -S-(thiadiazole-CH₂SO₃H) |
| 68 | thienyl | H | H | H | H | H | -S-(thiadiazole-CH₂SO₂CH₃) |

-continued

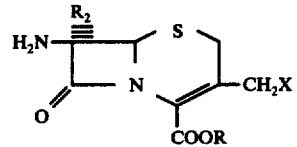

| Example | $R_1$ | $R_2$ | R | $R_3$ | $R_4$ | $R_5$ | X |
|---|---|---|---|---|---|---|---|
| 69 | thienyl | H | Na | H | H | H | -S-(1-cyanomethyltetrazolyl) |
| 70 | furyl | H | H | H | H | H | -S-(1-methyltetrazolyl) |

The acylating agents A may be in either the D- or L-form or may be a mixture of D- and L-isomers.

What is claimed is:

1. A compound of the formula

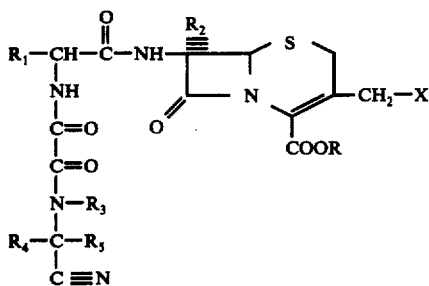

wherein R is hydrogen, lower alkyl, phenyl-lower alkyl, diphenyl-lower alkyl, tri(lower alkyl)silyl, tri(-lower alkyl)stannyl, trihaloethyl, aluminum, alkali metal, alkaline earth metal phenyl-lower alkyl amine, N, N-dibenzylethylene-diamine, lower, alkylemine, triethyamine, or N-lower alkyl piperdine; $R_1$ is phenyl, phenyl-lower alkyl, substituted phenyl wherein said phenyl substituent is one or two members selected from the group consisting of halogen, lower alkyl, lower alkoxy, and hydroxy, or a heterocyclic selected from the group consisting of 2-thienyl, 3-thienyl, 2-furyl and 3-furyl; $R_2$ is hydrogen or methoxy; $R_3$ is hydrogen, lower alkyl, phenyl-lower alkyl or cycloalkyl; $R_4$ and $R_5$ each is hydrogen or lower alkyl; and X is a heterothio group selected from the group consisting of

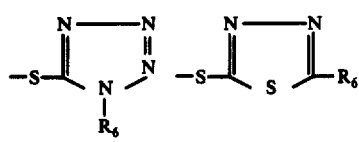

-continued (heterothio structures)

$R_6$ is hydrogen or lower alkyl; and $R_7$ is carboxy, $COO^\ominus$ ion $\oplus$, —COO-lower alkyl, $SO_3H$, —$SO_2$-lower alkyl or cyano.

2. A compound as in claim 1 wherein $R_1$ is thienyl.
3. A compound as in claim 1 wherein $R_1$ is phenyl.
4. A compound as in claim 1 wherein $R_1$ is furyl.
5. A compound as in claim 1 wherein X is methyltetrazolyl.
6. A compound as in claim 1 wherein R is hydrogen or alkali metal; $R_1$ is phenyl, thienyl or furyl; $R_2$ is hydrogen or methoxy; $R_3$, $R_4$ and $R_5$ each is hydrogen or lower alkyl; and X is as defined in claim 1.
7. A compound as in claim 1 wherein R is hydrogen, sodium or potassium; $R_1$ is phenyl or thienyl; $R_2$ is hydrogen; $R_3$ is hydrogen or methyl; $R_4$ and $R_5$ each is hydrogen and X is acetoxy or (1-methyl-1H-tetrazol-5-yl)thio.
8. A compound as in claim 1 wherein R, $R_2$, $R_3$, $R_4$ and $R_5$ each is hydrogen; $R_1$ is 2-thienyl; and X is (1-methyl-1H-tetrazol-5-yl)thio.

9. A compound as in claim 1 wherein R is sodium, $R_2$, $R_3$, $R_4$ and $R_5$ each is hydrogen; $R_1$ is 2-thienyl; and X is (1-methyl-1H-tetrazol-5-yl)thio.

10. A compound as in claim 1 wherein X is a heterothio group selected from the group consisting of

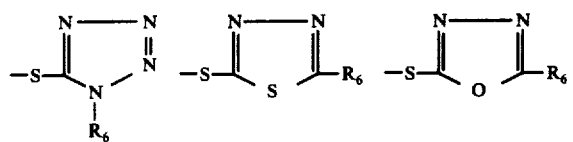

-continued

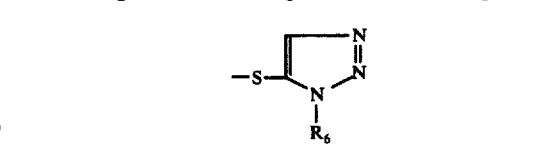

wherein $R_6$ is hydrogen or $C_1$-$C_4$-lower alkyl.

11. The D-isomer of a compound of claim 1.
12. The D-isomer of the compound of claim 8.
13. The D-isomer of the compound of claim 9.